United States Patent
Bush

Patent Number: 5,492,690
Date of Patent: Feb. 20, 1996

[54] BENZOYLACETATE ESTERS AS NON-SENSITIZING CHELATING PHOTO-PROTECTANTS

[75] Inventor: Rodney D. Bush, Fairfield, Ohio

[73] Assignee: The Procter & Gamble Company, Cincinnati, Ohio

[21] Appl. No.: 205,969

[22] Filed: Mar. 3, 1994

[51] Int. Cl.$^6$ .................................................. A61K 7/44
[52] U.S. Cl. ........................... 424/60; 514/675; 514/678; 514/680; 514/683; 514/688
[58] Field of Search ................... 514/675, 678, 514/683, 688, 690; 474/59, 60

[56] References Cited

U.S. PATENT DOCUMENTS

| | | | |
|---|---|---|---|
| 4,911,925 | 3/1990 | Shatkina | 424/401 |
| 5,152,983 | 10/1992 | Nambudiry | 424/60 |
| 5,292,529 | 3/1994 | Gregory | 424/59 |

FOREIGN PATENT DOCUMENTS

| | | | |
|---|---|---|---|
| 856814 | 7/1976 | Belgium. | |
| 431755A1 | 6/1991 | European Pat. Off.. | |
| 450892A1 | 10/1991 | European Pat. Off. | C07C 69/734 |
| 059069 | 3/1993 | Japan. | |
| 2137192 | 10/1984 | United Kingdom. | |

OTHER PUBLICATIONS

Bhanu et al "Conversion of 4–Phenyl Coremarius into Xanthones" CA 77:1620148 (1972).
Markov et al "On the Photosensitivity of Dibenzoyl Methane" CA 87:134299j (1977).
Patent Abstracts of Japan, vol. 11, No. 53 (C–404) (2500) Feb. 19, 1987: JP A,61 215 318 (Shiseido Co. Ltd.) Sep. 25, 1986.
Donnelly et al. "Structural Modifications of Dalbergin Using Benzeneseleninic Anhydride", *Heterocycles*, vol. 28, No. 1, pp. 411–419, (1989).
Chemical Abstract Registry No. 101126–46–9 CA 104:133291 (1985).

*Primary Examiner*—Ceila Chang
*Attorney, Agent, or Firm*—Loretta J. Henderson; John M. Howell; David L. Suter

[57] ABSTRACT

The subject invention relates to pharmaceutical compositions comprising a safe and effective amount of a compound having the structure:

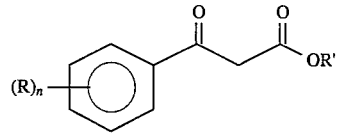

wherein n is 3 or 4; each R is independently alkyl or alkoxy; and R' is $C_1C_{20}$ alkyl; and a pharmaceutically-acceptable topical carrier.

The subject invention also relates to methods for preventing damage to skin, without markedly sensitizing the skin, by topically applying a safe and effective amount of such compounds to the skin.

12 Claims, No Drawings

৫,৪৯২,৬৯০

BENZOYLACETATE ESTERS AS NON-SENSITIZING CHELATING PHOTO-PROTECTANTS

TECHNICAL FIELD

The subject invention relates to topical pharmaceutical compositions useful for protecting the skin from the harmful effects of radiation, particularly ultraviolet radiation, such as sunburn and sun-induced premature aging of the skin. The subject invention involves compounds exhibiting activity both as absorbers of ultraviolet (UV) light and as metal chelators which inhibit production of free radicals. The subject invention further involves compounds exhibiting markedly reduced sensitization compared to existing photoprotectants.

BACKGROUND OF THE INVENTION

The damaging effects of radiation, particularly sunlight, on skin are well documented. Much damage is due to routine day-to-day activities in the sunlight.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin. Numerous epidemiologic studies demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed, Chapter 26, American Pharmaceutical Association, Washington, D.C., 1982, pp. 499–511; Grove and Forbes, "A Method for Evaluating the Photoprotection Action of Sunscreen Agents Against UV-A Radiation", *International Journal of Cosmetic Science*, Vol. 4 (1982), pp. 15–24; and U.S. Pat. No. 4,387,089 issued to DePolo on Jun. 7, 1983. Although the immediate effects of ultraviolet radiation may be cosmetically and socially gratifying, the long-term hazards are cumulative and sometimes serious.

Sunblock agents are commercially available to protect the skin from UV radiation. These agents scatter or reflect ultraviolet radiation. Examples include titanium dioxide and zinc oxide. However, these agents are very susceptible to rub-off or wear-off, resulting in little or no protection.

The most common agents for sun protection are sunscreens. These agents exert their effects through absorption of ultraviolet radiation so that it cannot penetrate the skin. Sunscreens must remain on the surface of the skin during exposure to be effective. However, sunscreens are easily rubbed off or washed off by sweating or swimming and can also be lost by penetration into the skin.

In developing a new sunscreen, it is important that the material be safe and effective. In particular, it is not feasible to use a material which sensitizes the skin. Certain sunscreens are effective for a one time useage, however, on reapplication they may cause dermatitis. This phenomenon is known as sensitization and is usually noted as a reddening of the skin, a rash-like condition. Since sunscreens are used repeatedly it is important for a sunscreen not to be a sensitizer.

It is an object of the subject invention to provide topical pharmaceutical compositions which provide protection against damage to the skin from sun exposure and other radiation sources.

It is also an object of the subject invention to provide topical pharmaceutical compositions which provide protection against damage to the skin from sun exposure and other radiation sources while inducing little or no skin sensitization.

It is a further object of the subject invention to provide methods for preventing damage to the skin due to exposure of the skin to the sun and other radiation sources.

It is a still further object of the subject invention to provide methods for preventing damage to the skin due to metal-catalyzed free radical generation in the cells of the skin.

It is a still further object of the subject invention to provide methods of protecting the skin from radiation sources without marked sensitization of the skin.

SUMMARY OF THE INVENTION

The subject invention relates to pharmaceutical compositions comprising a safe and effective amount of a compound having the structure:

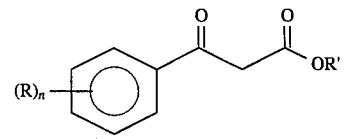

wherein n is 3 or 4, each R is, independently, alkyl or alkoxy; and R' is alkyl having from 1 to about 20 carbon atoms; and a pharmaceutically-acceptable carrier. The subject invention also relates to methods for preventing damage to skin by topically applying a safe and effective amount of such compounds to the skin.

DETAILED DESCRIPTION OF THE INVENTION

As used herein, "alkyl" means carbon-containing chains which may be straight, branched or cyclic; substituted or unsubstituted; saturated, monounsaturated (i.e., one double or triple bond in the carbon chain), or polyunsaturated (i.e., two or more double bonds in the carbon chain, two or more triple bonds in the carbon chain, one or more double and one or more triple bonds in the carbon chain). Unless otherwise indicated, alkyl are preferably as follows. Preferred alkyl are straight or branched chain, more preferably straight chain. Preferred alkyl are mono-, di-, or tri-, or unsubstituted, more preferably monosubstituted or unsubstituted, most preferably unsubstituted. Preferred alkyl are saturated or monounsaturated, more preferably saturated. Preferred alkyl are $C_1$–$C_8$, more preferably $C_1$–$C_6$, more preferably still $C_1$–$C_4$, more preferably still $C_1$–$C_2$, most preferably $C_1$.

As used herein, "substituted", in reference to alkyl groups, means such groups that can be mono- or polysubstituted. Preferred substituents are electron donating groups; preferred substituents are selected from the group consisting of halogen, hydroxy, amino, nitro, carboxy, thio, aryl, alkyl, alkoxy, and aryloxy.

As used herein, "aryl" means aromatic rings which may be unsubstituted or substituted. Preferred aryl are phenyl or naphthyl, especially phenyl. Preferred aryl are mono-, di-, tri- substituted or unsubstituted; more preferred aryl are monosubstituted or unsubstituted, especially unsubstituted. Preferred aryl substituents include alkyl, halo, amino, hydroxy, alkoxy, cyano, nitro and trifluoromethyl.

As used herein, "alkoxy" means O-alkyl.

As used herein, "aryloxy" means O-aryl.

As used herein, "safe and photoprotectively effective amount" means an amount sufficient to substantially reduce the deleterious effects of ultraviolet radiation to skin but not so much as to cause serious side effects or adverse skin reactions.

As used herein, "regulating" means preventing, retarding, or arresting.

As used herein, all percentages are by weight unless otherwise specified.

As used herein, "sensitizer" means a compound that is effective for a one-time usage, but causes dermatitis on repeated application. Sensitizers cause sensitization in skin, usually exhibited as a rash-like reddening of the skin.

Active Compound

The subject invention involves compounds, referred to herein as "active compounds", having the structure:

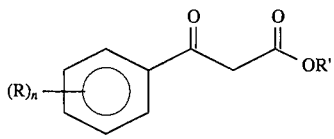

In structure (1), n is 3 or 4; preferred n is 4.

In structure (1), each R is, independently, alkyl or alkoxy. Preferred R is linear or branched alkyl or alkoxy having from 1 to about 5 carbon atoms. Preferred R is monosubstituted or unsubstituted. Preferred R is saturated. If substituted, the preferred substituents are alkyl, alkoxy, hydroxy or halo. More preferred R is straight chain. More preferred R are $C_1$–$C_4$ alkyl. More preferred R is unsubstituted. More preferred R are methyl or ethyl; most preferred R is methyl.

In structure (1), R' is linear, branched or cyclic, substituted or unsubstituted alkyl, having from 1 to about 20 carbon atoms. R' is preferably straight or branched chain $C_1$–$C_8$ more preferably $C_1$–$C_4$, more preferably still $C_1$–$C_2$, most preferably $C_1$, alkyl. R' is preferably unsubstituted; if substituted, preferred substituents include hydroxy and halo, especially fluoro and chloro. R' is preferably saturated.

The active compounds useful in the subject invention are generally moderate UV-light absorbers, but provide surprisingly high values in an SPF test (based on Test Method I hereinbelow). The active compounds are also good metal chelators and provide protection against chronic skin aging and wrinkling due to metal catalyzed free radical formation, which may be caused by skin exposure to UV-light or other causes. Therefore, the compositions of the subject invention which comprise the active compounds can provide excellent protection against both short term (acute) and long term (chronic) exposure to UV-light and against damage due to other causes of metal-catalyzed free radical formation.

It is important that sunscreens not be sensitizers since they are applied repeatedly. The compounds described in this application have surprisingly low sensitization as measured by the Murine Local Lymph Node Assay (Test II) and Guinea Pig Sensitization Test (Test III).

Active compounds useful in the subject invention also include metal complexes of the compounds of structure (1). The active compounds of structure (1) are metal chelators and readily form complexes with metal ions. The inclusion of metal complexed active compounds in the compositions of the subject invention can enhance the acute photoprotection provided by the composition, but may reduce the chronic photoprotection, since it may tie up a substantial portion of the chelating ability of the active compound. A metal ion generally complexes with from about 1 to about 4 molecules of an active compound of structure (1).

Preferred metal ions for inclusion in the metal complexed active compounds useful in the subject invention include sodium, aluminum, zinc, iron, lithium, magnesium, potassium, calcium, rubidium, strontium, titanium, zirconium, vanadium, chromium, manganese, cobalt, nickel, copper, gallium, scandium, silicon, boron, praseodymium, lanthanum, promethium, samarium, and europium; more preferred metal ions are those which do not have d-electrons: sodium, aluminum, zinc, lithium, magnesium, potassium, calcium and scandium; most preferred metal ions are sodium, aluminum, zinc, lithium, gallium and scandium.

Preferred active compounds useful in the subject invention include the following:

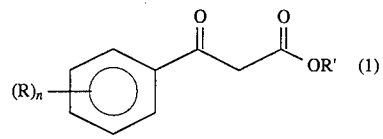

| # | Compound | Name |
|---|---|---|
| 1 | n = 4, R' = methyl | 1-(2',3',4',5'-tetramethylphenyl)-3-(methoxy)-propane-1,3-dione |
| 2 | n = 4, R' = ethyl | 1-(2',3',4',5'-tetramethylphenyl)-3-(ethoxy)-propane-1,3-dione |
| 3 | n = 4, R' = propyl | 1-(2',3',4',5'-tetramethylphenyl)-3-(propoxy)-propane-1,3-dione |
| 4 | n = 4, R' = butyl | 1-(2',3',4',5'-tetramethylphenyl)-3-(butoxy)-propane-1,3-dione |
| 5 | n = 4, R' = pentyl | 1-(2',3',4',5'-tetramethylphenyl)-3-(pentoxy)-propane-1,3-dione |
| 6 | n = 4, R' = hexyl | 1-(2',3',4',5'-tetramethylphenyl)-3-(hexoxy)-propane-1,3-dione |
| 7 | n = 4, R' = isopropyl | 1-(2',3',4',5'-tetramethylphenyl)-3-(iso-propoxy)-propane-1,3-dione |
| 8 | n = 3, R'= ethyl | 1-(2',3',4',-trimethylphenyl)-3-(iso-ethoxy)-propane-1,3-dione |
| 9 | n = 3, R'= propyl | 1-(2',3',4',-trimethylphenyl)-3-(iso-propoxy)-propane-1,3-dione |

R = methyl in preferred compounds 1–9 above.

The following example exemplifies the synthesis of active compounds useful in the subject invention.

EXAMPLE I 1-(2',3',4',5'-tetramethylphenyl)-3-(ethoxy)-propane-1,3-dione a) 2,3,4,5-Tetramethylbenzoic acid A 1 L 3-necked flask is equipped with a magnetic stirrer, argon inlet, addition funnel and thermowell. The flask is purged with argon then charged aluminum chloride (71.5 g, 0.536 mol) and methylene chloride (350 mL). The resulting suspension is cooled to 2° C. with an ice bath. The oxalyl chloride (68.1 mL, 0.536 mol) is transferred to the addition funnel under argon then added dropwise to the reaction over a 30 minute period. After complete addition the mixture is stirred at 2° C. for 15 minutes. The addition funnel is rinsed with methylene chloride (10 mL), and the 1,2,3,4-tetramethylbenzene (60.0 g, 0.477 mol) in methylene chloride (225 mL) is transferred to the addition funnel then added dropwise to the reaction over a 1.5 hour period while maintaining an internal temperature below 3° C. After complete addition the cooling bath is replaced by a heating mantle and the addition funnel with a condenser. The reaction is heated at reflux for 1.5 hours (HCl gas evolution stops), then cooled to room temperature. The reaction is quenched over a mixture of concentrated HCl (40 mL) and crushed ice/water (total volume 1.5 L). The product is extracted with methylene chloride (3×750 mL), dried over $MgSO_4$, clarified, then concentrated in vacuo to an off white residue. This residue is triturated in hexanes (400 mL) for 2 hours. The solid is collected on a filter, washed in situ with hexanes (2×50 mL) then dried to constant weight, 63.4 g (80% yield). Additional reactions are carried out to produce a total of 210 g of crude material. This material is recrystallized from refluxing absolute ethanol (1250 mL), to give 118.4 g of product. A second crop of material is obtained by concentrating the mother liquor and dissolving the resulting residue in refluxing absolute ethanol (600 mL) to give 63.7 g of material suitable for further transformation.

(b) 2.3.4.5-Tetramethylbenzoyl chloride

A 3 L 3-necked flask is equipped with a condenser, argon inlet, thermowell, magnetic stirrer. The flask is purged with argon then charged with 2,3,4,5-tetramethylbenzoic acid (138.3 g, 0.776 mol), methylene chloride (1.5 L), thionyl chloride (73.5 mL, 1.01 mol) and N, N-dimethylformamide (2.0 mL, 0.026 mol). The resulting suspension is heated to reflux, after a clear solution is formed, heating is continued for 3.5 hours. The solution is allowed to cool then concentrated in vacuo. Last traces of thionyl chloride are removed by co-distillation with toluene (2×100 mL). The remaining oil is dried under high vacuum then used without further purification. Additional reactions are carded out to produce a total of 218 g of 2,3,4,5-tetramethylbenzoyl chloride.

(c) 1-(2',3',4',5'-Tetramethylphenyl)-3-(ethoxy)-propane-1,3-dione

A 5 L, 3-necked flask is equipped with an overhead stirrer, addition funnel, thermowell and argon inlet. The flask is purged with argon then charged with ethyl hydrogen malonate (139.8 g, 1.06 mol) and tetrahydrofuran (2.3 L). The flask is cooled to −65° C. in a dry-ice/acetone bath. The n-butyllithium (892 mL, 2.23 mol) is transferred to the addition funnel then added dropwise to the stirred solution over a 2 hour period. After complete addition the reaction is warmed to −5° C. and stirred for 15 minutes. The resulting thick slurry is cooled to −65° C. The addition funnel is rinsed with tetrahydrofuran (20 mL) and the 2,3,4,5-tetramethylbenzoyl chloride (152.6 g, 0.776 mol) in tetrahydrofuran (250 mL) is transferred to the addition funnel under argon then added dropwise to the reaction over a 1.5 hour period. After complete addition the mixture is stirred at −65° C. for 1.5 hours. The reaction is allowed to warm to −20° C. then quenched over a water-ice mixture (3 L total volume). The solution is acidified to pH 2 by the slow addition of concentrated HCl. The product is extracted with ether (3×1 L), washed with saturated $NaCO_3$ (2×1.5 L) and brine (1×1.5 L), dried over $MgSO_4$, then concentrated in vacuo to a tan oil. An additional reaction is carried to produce a total of 185.1 g of crude product. Attempts to purify this material by vacuum distillation result in the apparent partial decomposition of the product. The remaining material is divided into two portions with each being chromatographed over 2 kg of silica eluted with methylene chloride. The TLC pure fractions are combined, concentrated in vacuo at 40° C. to constant weight, 108.5 g (42% yield).

See also Hart. H., and R. W. Fish., *J. Am. Chem. Soc.*, Vol 83, p. 4460, (1961); Smith, L. I., and S. A. Harris, *J. Am. Chem. Soc., Vol.* 35, p. 1289, (1935); and Sokol, P. E. *Org. Synthesis*, Coll. Vol. 5, p. 706 (1973), incorporated herein by reference.

Other compounds of interest having different R substituents on the phenyl ring can be synthesized by similar reactions with the appropiately substituted benzenes in place of 1,2,3,4-tetramethylbenzene. Other compounds of interest having different R' moieties can be synthesized by use of other esters of ethyl hydrogen malonate e.g. propyl hydrogen malonate, butyl hydrogen malonate etc.

Compositions of the subject invention comprise a safe and effective amount of an active compound useful in the subject invention disclosed hereinabove, preferably from about 0.1% to about 25%, more preferably from about 0.5% to about 10%, more preferably still from about 1% to about 5%.

In addition to the active compound, the compositions of the subject invention comprise a topical pharmaceutically-acceptable carrrier. The term "pharmaceutically-acceptable carrier", as used herein, means one or more compatible solid or liquid filler diluents or encapsulating substances which are suitable for administration to a human or lower animal. Such carriers must be of sufficiently high purity and sufficiently low toxicity to render them suitable for administration to the human or lower animal being treated. Such carrier preferably comprises from about 75% to about 99.9%, more preferably from about 90% to about 99.5%, more preferably still from about 95% to about 99% of the composition.

Topical Carriers

The topical compositions of the subject invention may be made into a wide variety of product types. These include, for example, lotions, creams, beach oils, gels, sticks, sprays, ointments, pastes, mousses and cosmetics. These product types may comprise either of two basic types of carrier systems, solutions and emulsions.

The topical compositions of the subject invention formulated as solutions typically include a pharmaceutically-acceptable aqueous or organic solvent. Preferred solvents, in addition to being capable of having dispersed or dissolved therein the active compound, also possesses acceptable safety (e.g., irritation and sensitization characteristics), as well as good aesthetic properties (e.g., does not feel greasy or tacky). Water is a typical aqueous solvent. Examples of suitable organic solvents include: propylene glycol, polyethylene glycol (200–600), polypropylene glycol (425–2025), glycerol, 1,2,4-butanetriol, sorbitol esters, 1,2, 6-hexanetriol, ethanol, isopropanol, butanediol, and mixtures thereof. Preferred solutions of the subject invention contain from about 0.01% to about 20%, more preferably from about 0.5% to about 10%, more preferably from about 1% to about 5% of the active compound, and from about 80% to about 99.99%, more preferably from about 90% to about 99.5%, more preferably from about 95% to about 99% of an acceptable organic solvent.

If the topical compositions of the subject invention are formulated as an aerosol and applied to the skin as a spray-on, a propellant is added to a solution composition. A more complete disclosure of propellants useful herein can be found in Sagarin, *Cosmetics Science and Technology*, 2nd Edition, Vol. 2, pp. 443–465 (1972).

Topical compositions of the subject invention may be formulated as a solution comprising an emollient. An example of a composition formulated in this way would be a beach oil product. Such compositions typically comprise from about 0.01% to about 20%, preferably from about 0.1% to about 10%, more preferably from about 0.5% to about 5% of the active compound and from about 1% to about 50%, preferably from about 5% to about 20% of a topical pharmaceutically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 0.1% to about 20%, preferably from about 0.5% to about 10%, of the active compound; from about 1% to about 20%, preferably from about 5% to about 10%, of an emollient; and from about 50% to about 90%, preferably from about 60% to about 80%, water.

Another type of product that may be formulated from a solution carrier system is a cream. A cream of the subject invention would comprise from about 0.1% to about 20%, preferably from about 0.5% to about 10%, of the active compound; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may also comprise from about 2% to about 10% of an emollient plus from about 0.1% to about 2% of a thickening agent. A more complete disclosure of thickening agents useful herein can be found in Sagarin, *Cosmetics, Science and Technology*, 2nd Edition, Vol. 1, pp. 72–73 (1972).

If the carrier is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al,; U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference. Preferred emulsifiers are anionic or nonionic, although the other types may also be used.

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the subject invention. In general, such single or multiphase emulsions contain water, emollients and emulsifiers as essential ingredients.

Triple emulsion carrier systems comprising an oil-in-waterin-silicone fluid emulsion composition as disclosed in U.S. patent application Ser. No. 022,876, Figueroa, et al., filed Mar. 6, 1987, herein incorporated by reference, are also useful in the subject invention. This triple emulsion carrier system can be combined with from about 0.1% to about 20%, preferably from about 0.5% to about 10%, of the active compound to yield the topical pharmaceutical/cosmetic composition of the subject invention.

Another emulsion carrier system useful in the topical compositions of the subject invention is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan monofatty acid (commercially available under the trade name Tweens) or other nonionics; and from about 7% to about 20% water. This carrier system is combined with from about 0.5% to about 10% of the active compound.

Lotions and creams can be formulated as emulsions as well as solutions. Typically such lotions comprise from about 0.1% to about 20%, preferably from about 0.5% to about 10%, of the active compound; from about 1% to about 20%, preferably from about 5% to about 10%, of an emollient; from about 25% to about 75%, preferably from about 45% to about 95%, water; and from about 0.1% to about 10%, preferably from about 0.5% to about 5%, of an emulsifier. Such creams would typically comprise from about 0.1% to about 20%, preferably from about 0.5% to about 10%, of the active compound; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

If the topical compositions of the subject invention are formulated as a gel or a cosmetic stick, a suitable amount of a thickening agent, as disclosed supra, is added to a cream or lotion formulation.

The topical compositions of the subject invention may also be formulated as makeup products such as foundations, or lipsticks.

The topical compositions of the subject invention may contain, in addition to the aforementioned components, a wide variety of additional oil-soluble materials and/or water-soluble materials conventionally used in topical compositions, at their art-established levels.

Various water-soluble materials may also be subject in the compositions of this invention. These include humectants, proteins and polypeptides, preservatives and an alkaline agent. In addition, the topical compositions herein can contain conventional cosmetic adjuvants, such as dyes, opacifiers (e.g., titanium dioxide), pigments and perfumes.

The topical compositions of the subject invention may also include a safe and effective amount of a penetration enhancing agent. A safe and effective amount is generally from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European Patent Application 0043738, Cooper et al., published Jan. 13, 1982.

Other conventional skin care product additives may also be included in the compositions of the subject invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the subject invention. For example, Vitamin A, and derivatives thereof, Vitamin $B_2$, biotin, pantothenic, Vitamin D, Vitamin E and mixtures thereof may be used.

Compositions of the subject invention can be tested using the following test methods to determine effective dosage levels of the active compound and appropriate formulations and methods of application. For example, if an active compound from Test Method I is not effective in a given formulation, it may be due to inability of the agent to penetrate the skin from the formulation. A formulation with a skin penetration enhancer may be needed in order to achieve the desired result.

Test Method I

Guinea Pig SPF Method

The guinea pig is used as a model for determination of sun protection factor (SPF) values of topical protective agents; see, e.g., Leroy, D. & P. Deschamps, "Sunscreen Seawater Resistance: Comparison of Human and Guinea-pig Test Models", *Photodermatol.*, Vol. 2 (1985), pp. 38–40; and Bissett, D. L., J. F. McBride, D. P. Hannon, & L. F. Patrick, "Time-dependent Decrease in Sunscreen Protection Against Chronic Photodamage in UVB-irradiated Hairless Mouse Skin", *J. Photochem. Photobiol. B: Biol.*, Vol. 9 (1991), pp. 323–334; and "Sunscreen Drug Products for Over-the-counter Human Drugs", *Federal Register* (Food and Drug Administration), Vol. 43 (1978) p. 38259; all of which are incorporated herein by reference. This animal develops an erythemal response to UV radiation which is very similar to the human response, and photoprotective agent SPF values are similar in the two species.

Materials and Methods

Animals—Male Hartley strain guinea pigs are obtained from Charles River Laboratories, Portage, Mich. The guinea pigs weigh approximately 300 g at the start of experimental work. All animals are housed in individual cages in a room with controlled temperature and humidity and with a 12-hour light/darkness cycle. They are given a standard Purina Chow diet and water ad libitum.

UV Radiation Source and Radiometer—A model 81172 Oriel Corp. (Stratford, Conn.) solar simulator equipped with a 1000-watt zenon arc ozone-free lamp is used. Schott Glass Technologies, Inc. (Duryea, Pa.) filters (a 3-mm WG-305 (to remove UVC) and a 1-mm UG-5 filter (to remove visible light)) are inserted in the light path just past the simulator output port to simulate the solar UV spectrum. Total UVB or UVA output is determined with an International Light (Newburyport, Mass.) model IL1350 radiometer equipped with SED 240 (UVB) and SED 015 (UVA) sensors. Spectral scans are recorded on a model 4950 strip chart recorder (Bausch & Lomb, Austin, Tex.) using an International Light double monochrometer spectro-radiometer system (model IL 700A/760/791).

Guinea Pig SPF Measurements—The dorsal skin of guinea pigs is shaved with electric clippers and then depilated with NeetR Lotion Hair Remover (Whitehall Laboratories, New York, N.Y.). The skin is rinsed under warm tap water and dried with a towel. Sixteen hours later, the dorsal skin is treated with 2 mg/cm2 of test material solution.

The animals (n=5 per treatment group) are then wrapped with 3-inch wide tape (ElastoplastR, Beiersdorf Inc., Norwalk, Conn.) containing four 2-cm diameter exposure windows (two windows on each side of the spinal area). The adhesive side of the tape covering the dorsal skin area is coated with black construction paper to prevent reddening of the skin from adherence of the tape to that skin region. The time between topical treatment and irradiation with UV-light is approximately 15 minutes.

Animals are restrained with a neck clip and exposed individually. Each animal is positioned with its dorsal skin surface 18 inches below the filter set of the solar simulator. The irradiance at this distance is approximately 0.45 mW/cm$^2$ UVB and 10.2 mW/cm$^2$ UVA. Irradiation times of the four exposure windows on each animal are set to bracket the suspected SPF of the material being tested. Exposure windows are covered with opaque tape at the end of each time point. At the completion of all irradiations, all tape is removed from the animals.

Erythema is scored (0–3 grading scale, with half grade increments) 24 hours later, using non-exposed adjacent skin on each animal as no UV control (score=0). A grade of 1.0 (detectable redness over the entire exposure area) is considered 1 MED. SPF is then calculated from the ratio: (UV dose to achieve 1 MED with test material)/(UV dose to achieve 1 MED without test material).

Test Method II

Local Lymph Node Assay

Animals: Female CBA/J mice are obtained from Jackson Laboratory, Bar Harbor, Me., weighing approximately 17 to 26 grams and are randomized for selection for the study. The mice are 6–9 weeks of age at experiment initiation. Five mice per group are used for all test groups.

Experimental Design: Each control or treatment group consists of five animals. The induction period consists of treating the animals once a day for four consecutive days with the article. Approximately 24±2 hours between applications of test article is maintained. On day five the animals are given intravenous (i.v.) injections of [3H]-thymidine (18 to 24 hours after the last application of test article to the ears). Five hours after the i.v. injections, the animals are euthanized and the auricular nodes removed. Single cell suspensions of the node cells are prepared and then counted on a liquid scintillation counter to quantitate [3H]-thymidine incorporation. Application of Test Article: The animals are restrained in such a manner as to allow free access to the dorsal and ventral sides of both ears. Using an adjustable push button pipet (Rainin Pipetman® or equivalent), 12.5 μl of the test article is applied to the dorsal and ventral sides of each ear, for a total of 25 μl of test article per ear. Care is taken to ensure that the test article does not run off the ear during application. Pipets are calibrated at least every three months (90 days) to assure accurate delivery of the 0.0125 ml volume.

Intravenous Injection of [3H]-Thymidine: Each animal receives 0.250 ml of phosphate buffered saline (PBS) containing 20 µCi of [3H]-thymidine (specific activity of 6.7 Ci/mmol). A heat lamp may be used to dilate the tail veins for easier i.v. injections. The animal is restrained in such a manner as to allow complete access to the tail. A 1 cc disposable syringe and 25–27 gauge needle may be used for i.v. injections. An animal is excluded from the study if the full 0.250 ml of [3H]-thymidine/PBS is not properly i.v. injected. Statistical analysis is not performed on a group when more than one mouse is excluded from the group.

Lymph Node Removal: Five hours after the [3H]-thymidine injections, the animal is euthanized with $CO_2$ and the auricular lymph nodes removed. Care is taken to assure that the intact lymph nodes are removed. Once the lymph nodes are removed, they are placed in a 12–75 mm capped tissue culture tube (approximately 4.5 ml capacity) containing 4 ml of PBS.

Single Cell Suspension: The lymph nodes are transferred to a 60 mm tissue culture dish by pouring the PBS from the tubes containing the lymph nodes. Both the top and bottom of the tissue culture dish may be used for preparing single cell suspensions for each individual animal. The lymph nodes are placed onto an approximately 1 inch square section of nylon macromesh (mesh opening ~100 microsn, ~85 microns thick) with a small amount of PBS (0.5–1.5 ml). The capsule is snipped with a small pair of pointed surgical scissors and the nodes are gently rubbed through the nylon screen using the rubber surface of a plunger from a 1 cc disposable syringe. A Pasteur pipet and a small pair of forceps are used to rinse the screen with PBS into the bottom portion of the tissue culture dish. The nylon filter is discarded after rinsing and the tissue culture dish rinsed with the PBS. The PBS is placed back into the 12×75 mm round bottom tube to allow the capsule debris to settle to the bottom. After approximately 5 minutes the PBS is carefully drawn off with a Pasteur pipet and placed in a 15 ml conical bottom centrifuge tube containing 6 ml of PBS (approximately 10 ml total tube volume) and the cell suspensions centrifuged at 200×g for 10 minutes. After the first washing with PBS the cells are resuspended in 10 ml of PBS, and a second wash is performed. After completion of the second wash, the cells are suspended in 3 ml of 5% trichloroacetic acid (TCA) (w/v, distilled $H_2O$) and left at approximately 4° C. for 18 to 72 hours.

Preparation for Scintillation Counting: The cell suspension is centrifuged at 200×g for 10 minutes and resuspended in 1 ml of 5% TCA. Scintillation vials (borosilicate, 20 ml volume) containing 10 ml of Ecolulme scintillation cocktail are appropriately labeled with the individual animal numbers. The individual cell suspensions are transferred into the appropriate vials along with an additional 1 ml of TCA which has been used to rinse the bottom portion of the tube. The TCA and scintillation fluid are thoroughly mixed by gently swirling the contents of the vial until the solution becomes clear. Scintillation Counting; A liquid scintillation system is used for counting. The samples are counted for 5–10 minutes and the counts recorded in disintegrations per minute (DPM). The scintillation numbers are compared to controls to indicate the degree of activation of the immune system which is indicative of sensitization.

Test Method III

Guinea Pig Sensitization Testing: Modified Buehler Method

Animals: Hartley outbred guinea pigs are used. Whenever possible, equal numbers of males and females are used. 20 test animals are used, 10 control animals for primary challenge, and 10 control animals for rechallenge. All animals, including rechallenge is controls, weigh 300–500 grams at the start of the study.

In addition, a total of 12 animals are used for induction and challenge irritation screens for each test substance. These animals weigh 300–500 grams when used. Body weights for these irritation screen animals are obtained up to 24 hours prior to patching of the animals.

Treatment and Observation Methods

Patching Method: The identical patching method is used for induction, irritation screens, challenge and rechallenge.

To prevent skin irritation and/or nicking of the skin, a sharp clipper blade is used to carefully clip the fur from the test site area. The animals' fur is shaved the day before exposure with a fine clipper blade #80, size 40 Oster or equivalent. Closed patches are applied to the animals as follows:

0.4 ml of a test substance or freshly prepared solution are applied on a 20×20 mm Webril pad affixed to adhesive tape. (Professional Medical Products, Inc., Greenwood, S.C., product *33-4022-1).

0.3 ml of a test substance or freshly prepared solution are applied in a 25 mm Hill Top Chamber®.

The animal is put in the restrainer and the designated patch applied to the clipped surface as quickly as possible after the substance has been applied. The patch appliance is occluded with a rubber dental dam. The rubber dam used for occlusion of the patches is a medium gauge 5 or 6 inches wide, depending on the animal size and the number of patches to be covered. The rubber dam is pulled snugly on each side of the animal and secured with at least one clip on each side of the restrainer. The rubber dam is placed under the front and back metal restrainer hoods. The dental dam is stretched slightly to make even contact with the animal over the entire dorsal surface without wrinkling the dental dam. The restrainer is adjusted to minimize movement of the animal during the exposure period.

The animals are observed for any signs of distress, and the restrainer or dental dam adjusted for maximum comfort without interfering with necessary test conditions. The animals are monitored for distress at regular (60 to 90 minutes) intervals, during the restraint period.

The animals are returned to their cages without rinsing.

Grading Method: The identical grading method is used for irritation screens and challenge.

Eighteen to twenty-two (18–22) hours after patches have been removed, all animals are depilated with Neet Cream or Lotion Hair Remover (Whitehall Laboratories, Inc., New York). The depilatory is placed on the patch sites and surrounding areas, and left on for no more than fifteen (15) minutes. The depilatory is thoroughly washed off with a gentle spray or stream of warm, running water, the animals are dried with a towel, cloth or paper, and returned to their cages.

Two (2) to four (4) hours after depilation, the test sites are graded on a scale of 0 to 3 as follows:

0=no reaction

±=slight, patchy erythema (i.e., barely perceptible or questionable reaction)

1=slight confluent erythema (i.e., a slight but definite reaction at the patch site) or moderate, but patchy erythema (i.e., moderate erythema involving at least 50% or more of the area of the patch site)

2=moderate confluent erythema

3=severe erythema with or without edema

The grading is repeated 24 hours (±2 hours) later. This is defined as the 48-hour grade.

For rechallenge, all animals are depilated, eighteen to twenty (18–20) hours after patches have been removed with Magic Shave Powder, regular strength (Carson Products Company, Savannah, Ga.). The powdered depilatory is mixed with warm water, 125 to 150 ml of water per 5 oz. (141.5 gm container) of Magic Shave until a uniform slurry is attained and the depilatory is applied to the patch sites and surrounding areas and left on for no more than five (5) minutes. The depilatory is thoroughly washed off with a gently spray or stream of warm running water, the animals dried with a towel, paper or cloth, and returned to their cages.

Three (3) to four (4) hours after depilation, the test sites are graded on a scale of 0 to 3 as indicated above for irritation screens and challenge.

Combination Actives

A. Sunscreens

Optimum protection against sun damage can be obtained by using a combination of the active compounds of the subject invention together with sunscreens or sunblocks. Useful sunblocks include, for example, zinc oxide and titanium dioxide.

If the photoprotecting capability of the active compound is primarily active against UVB radiation, a combination of the active compound with a UVA sunscreen would be most desirable. Conversely, if the active compound is primarily active against UVA radiation, a combination of the active compound with a UVB sunscreen would be most desirable. Additional UVA and/or UVB protection may also be included in such compositions. The inclusion of sunscreens in compositions of the subject invention at low levels will not significantly reduce the tanning response of the user but will enhance immediate protection against acute UV damage.

A wide variety of conventional sunscreening agents are suitable for use in combination with the active compounds. Sagarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxy-naphthoic acid and its salts; o- and phydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid; tannic acid and its derivatives (e.g., hexaethylether); (butyl carbotol) (6-propyl piperonyl) ether; hydroquinone; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, 4-isopropyldibenzoylmethane; t-butylmethoxydibenzoylmethane; etocrylene; and 4-isopropyldibenzoylmethane.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-(bis(hydroxypropyl))aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylamino-benzoate, 2-phenylbenzimidazole-5-sulfonic acid, 2-(p-dimethylaminophenyl)- 5-sulfonicbenzoxazoic acid, 7-diethylamino-4-methylcoumarin and mixtures of these compounds, are particularly useful.

Preferred sunscreens useful in the compositions of the subject invention are 2-ethylhexyl p-methoxycinnamate, butylmethoxydibenzoylmethane, 2-hydroxy-4-methoxybenzophenone, octyldimethyl p-aminobenzoic acid and mixtures thereof.

A safe and photoprotectively effective amount of sunscreen may be used in the compositions of the subject invention. The sunscreening agent must be compatible with the active compound. Generally the composition may comprise from about 1% to about 20%, preferably from about 2% to about 10%, of a sunscreening agent. Exact amounts will vary depending upon the sunscreen chosen and the desired Sun Protection Factor (SPF). Because of the photoprotecting capability of the active compound against erythema, the combination provides an SPF greater than that of the sunscreen alone.

Also particularly useful in the subject invention are sunscreens such as those disclosed in U.S. Pat. No. 4,937,370 issued to Sabatelli on Jun. 26, 1990, and in U.S. Pat. No. 4,999,186 issued to Sabatelli and Spirnak on Mar. 12, 1991, both incorporated herein by reference. The sunscreening agents disclosed therein have, in a single molecule, two distinct chromophore moieties which exhibit different ultraviolet radiation absorption spectra. One of the chromophore moieties absorbs predominantly in the UVB radiation range and the other absorbs strongly in the UVA radiation range.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

The compositions of the subject invention, with or without sunscreens, may also be formulated as shampoos, conditioners, mousses or other hair care products. It is known that UV radiation damages hair and the photoprotecting agents of the subject invention may minimize such damage. Furthermore such formulations will provide a means for applying the photoprotecting agents of the subject invention onto the scalp, which is also susceptible to UV damage. Any compatible art-recognized hair care formulations can be used with the active compound added at a level of from about 1% to about 5%. If desired, a sunscreen may also be included at from about 1% to about 5%.

An agent may also be added to any of the compositions of the subject invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference.

B. Anti-Inflammatory Agents

In a preferred photoprotection composition of the subject invention, an anti-inflammatory agent is included as an active along with the active compound. The inclusion of an anti-inflammatory agent enhances the photoprotection benefits of the compositions. The anti-inflammatory agent protects strongly in the UVA radiation range (though it also provides some UVB protection as well). The topical use of anti-inflammatory agents reduces photo-aging of the skin resulting from chronic exposure to UV radiation. (See U.S. Pat. No. 4,847,071, Bissett, Bush, and Chatterjee, issued Jul. 11, 1989; and U.S. Pat. No. 4,847,069, Bissett and Chatterjee, issued Jul. 11, 1989, both incorporated herein by reference.) It has also been discovered that the combination of an anti-inflammatory agent and the active compound provides greater photoprotection than is provided by each active alone.

A safe and effective amount of an anti-inflammatory agent may be added to the compositions of the subject invention, generally from about 0.1% to about 10%, preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, fluclorondie, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the subject invention is hydrocortisone.

A second class of anti-inflammatory agents which is useful in the compositions of the subject invention includes the nonsteroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Antiinflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), both incorporated herein by reference.

Specific non-steroidal anti-inflammatory agents useful in the composition of the subject invention include, but are not limited to:

1) the oxicams, such as piroxicam, isoxicam, tenoxicam, sudoxicam, and CP-14,304;

2) the salicylates, such as aspirin, disalcid, benorylate, trilisate, safapryn, solprin, diflunisal, and fendosal;

3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac;

4) the fenamates, such as mefenamic, meclofenamic, flufenamic, niflumic, and tolfenamic acids;

5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenybutazone, oxyphenbutazone, feprazone, azapropazone, and trimethazone. Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the non-steroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Another class of anti-inflammatory agents which are useful in the subject invention are the anti-inflammatory agents disclosed in U.S. Pat. No. 4,708,966, Loomans et al., issued Nov. 24, 1987. This patent discloses a class of non-steroidal anti-inflammatory compounds which comprise specifically substituted phenyl compounds, especially substituted 2,6-di- tert-butyl phenol derivatives. For example, compounds selected from 4-(4'-pentyn-3'-one)-2, 6-di-t-butylphenol; 4-(5'-hexynoyl)- 2,6-di-t-butylphenol; 4-((S)-(–)-3'-methyl-5'-hexynoyl)-2,6-di-t-butylphenol; 4-((R)-(+ )-3'-methyl-5'-hexynoyl)-2,6-di-t-butylphenol; and 4-(3',3'-dimethoxypropionyl)- 2,6-di-t-butylphenol are useful in the subject invention.

Yet another class of anti-inflammatory agents which are useful in the subject invention are those disclosed in U.S. Pat. No. 4,912,248, Mueller, issued Mar. 27, 1990. This patent discloses compounds and diastereomeric mixtures of specific 2-naphthyl- containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen- (R)-2-butyl ester, and diasteromeric mixtures of (S)-naproxol- (R)-2-methyl butyrate and (S)-naproxol(S)-2-methyl butyrate are useful in the subject invention.

Finally, so-called "natural" anti-inflammatory agents are useful in the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

An even more preferred composition of the subject invention comprises an active compound, a sunscreen, and an anti-inflammatory agent together for photoprotection in the amounts disclosed for each individually hereinabove.

The photoprotection compositions of the subject invention may comprise, in addition to the active compound, a safe and photoprotectively effective amount of a radical scavenging compound, generally from about 1% to about 20%, preferably from about 2% to about 10%, more preferably from about 3% to about 5% of the composition. Examples of such radical scavenging compounds are ascorbic acid (Vitamin C) and its salts, tocopherol (Vitamin E), other tocopherol esters, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxyfumaric acid and its salts. Each of these compounds has photoprotecting capabilities. The use of the radical scavenger tocopherol sorbate in the subject invention in combination with the active compound is preferred.

C. Anti-Oxidants/Radical Scavengers.

In a preferred photoprotection composition of the subject invention, an anti-oxidant/radical scavenger is included as an active along with the active compound. The inclusion of an anti-oxidant/radical scavenger increases the photoprotection benefits of the composition.

A safe and photoprotectively effective amount of an anti-oxidant/radical scavenger may be added to the compositions of the subject invention, generally from about 0.1% to about 10%, preferably from about 1% to about 5%, of the composition.

Anti-oxidants/radical scavengers such as ascorbic acid (vitamin C) and its salts, tocopherol (vitamin E), tocopherol sorbate, other esters of tocopherol, butylated hydroxy benzoic acids and their salts, 6-hydroxy-2,5,7,8-tetramethyl-chroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used.

In a preferred photoprotection composition of the subject invention, compositions comprise one, any two, or all three of a sunscreening agent, anti-inflammatory agent, and/or an anti-oxidant/radical scavenging agent included as actives along with the active compound. The inclusion of two or all three of these agents with the active compound increases the photoprotection benefits of the composition.

Method For Preventing Deleterious Effects Caused By UV Exposure

The subject invention further relates to a method for protecting the skin of humans and lower animals from the deleterious effects of radiation, particularly UV radiation, and/or other causes of metal-catalyzed free radical production in the skin tissue. Such protection by the active compound extends to damage resulting from acute UV exposure, e.g. erythema. It also extends to protection from damage resulting from chronic UV exposure, e.g. photoaging. Such protection also extends to damage resulting from sources of radiation other than the sun; non-limiting examples include ultraviolet lights (e.g., tanning lights), X-rays, lasers, etc.

Such a method comprises applying to the skin of the human or lower animal a safe and effective amount of the active compounds disclosed hereinabove to be useful in the subject invention. This may be accomplished by using a composition comprising the active compound as disclosed hereinabove. The active compounds involved in each of the following methods may be simply spread over the skin, or rubbed into the skin to enhance penetration of the active compound. The active compounds are preferably applied in conjunction with UV exposure, i.e., prior to, during, or after UV exposure. More specifically, the active compounds are preferably applied from several hours, preferably up to 4 hours, prior to UV exposure, to up to 30 minutes after UV exposure, or anytime in between.

For protection against acute damage from UV radiation, topical application of the active compounds prior to exposure of the skin to UV radiation is preferred.

For protection against chronic damage from UV radiation, topical application of the active compounds is preferably done on a chronic basis. The active compounds are preferably topically applied to the skin about daily, preferably prior to substantial exposure of the skin to UV radiation. Such application preferably occurs from at least about once weekly to about 5 times daily, more preferably about once or 2 times daily, but for particularly effective compositions preferably once daily. Such application preferably occurs over long periods of time, preferably for more than one month, more preferably for more than six months, more preferably still for more than one year, 5 years, 10 years or more.

Typically a safe and photoprotectively effective amount of an active compound is from about 0.001 mg to about 1.0 mg, preferably from about 0.01 mg to about 0.5 mg, more preferably from about 0.05 mg to about 0.1 mg of the active compound per $cm^2$ skin.

A preferred method of the subject invention for preventing deleterious effects caused by UV exposure involves applying both a safe and photoprotectively effective amount of an active compound and a safe and photoprotectively effective amount of one or more of an additional sunscreening agent, an anti-inflammatory agent, and/or a radical scavenging compound (as defined hereinbefore) to the skin simultaneously. By "simultaneous application" or "simultaneously" is meant applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.01 mg to about 1.0 mg, preferably from about 0.05 mg to about 0.5 mg, per $cm^2$ of skin. The amount of radical scavenging compound applied is generally from about 0.01 mg to about 1.0 mg, preferably from about 0.05 mg to about 0.5 mg, per $cm^2$ skin. The amount of anti-inflammatory agent is generally from about 0.005 mg to about 0.5 mg, preferably from about 0.01 mg to about 0.1 mg.

The following examples further describe and demonstrate the preferred embodiments within the scope of the subject invention. The examples are given solely for the purpose of illustration, and are not to be construed as limitations of the subject invention since many variations thereof are possible without departing from its spirit and scope.

EXAMPLE 2

A moisturizing lotion is prepared by combining the following components utilizing conventional mixing techniques.

| Components | Percent by Weight of Composition |
|---|---|
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Tetrasodium EDTA | 0.10 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 2.00 |
| $C_{12}$–$C_1$ % Alcohol Benzoate (Finsolv TN - commercially available from Finetex, Inc.) | 2.00 |
| 1-(2',3',4',5'-tetramethylphenyl)-3-(ethoxy)-propane-1,3-dione | 2.00 |
| Dimethicone | 0.30 |
| Imidazolidinyl Urea | 0.10 |
| Ethylene Acrylate Copolymer | 3.80 |
| Tyrosine | 0.10 |
| Water | q.s. |

This lotion may be topically applied to inhibit damage caused by radiation, particularly acute or chronic UV exposure. Use of an amount of lotion sufficient to deposit about 0.5 mg/cm² of 1-(2',3',4',5'-tetramethylphenyl)-3-(ethoxy)-propane- 1,3-dione to the skin is appropriate.

EXAMPLES 3 & 4

Skin lotions are prepared by combining the following components utilizing conventional mixing techniques.

| Component | Percent by Weight of Composition | |
|---|---|---|
| | Example 3 | Example 4 |
| 4-N,N-(2-Ethylhexyl)methylamino-benzoic Acid Ester of 4-(2-Hydroxyethoxy)-dibenzoylmethane | 5.00 | — |
| Dimethyl Isosorbide | 5.00 | — |
| Dioctyl Maleate | 8.00 | 2.00 |
| $C_{12}$–$C_1$ % Alcohol Benzoate (Finsolv TN-commercially available from Finetex, Inc.) | 4.00 | 2.00 |
| Glycerin | 3.50 | 3.50 |
| Ethylene Acrylate Copolymer | 3.80 | 3.80 |
| 1-(2',3',4',5'-tetramethylphenyl)-3-(propoxy)-propane-1,3-dione | 2.00 | 1.00 |
| Cetyl Alcohol | 1.75 | 1.75 |
| Polyoxyethylene Stearyl Alcohol (commercially available in the Brij series from ICI Americas, Inc.) | 1.75 | 1.75 |
| Stearic Acid | 1.25 | 1.25 |
| Glyceryl Stearate | 1.13 | 1.13 |
| Alkyl Parabens | 0.90 | 0.90 |
| Titanium Dioxide | 0.40 | — |
| Dimethicone | 0.30 | 0.30 |
| Carbomer viscosity control agents (commercially available as Acritamer from R.I.T.A. Corp.) | 0.23 | 0.23 |
| Imidazolidinyl Urea | 0.10 | 0.10 |
| Potassium Hydroxide | 0.15 | 0.15 |
| Tyrosine | 0.10 | 0.10 |
| Pentasodium diethylenetriamine-pentaacetic acid or tetrasodium ethylenediamine tetraacetic acid | 0.10 | 0.10 |
| Water | q.s. | q.s. |

These lotions are useful for topical application to inhibit damage caused by radiation, particularly acute or chronic UV exposure. Use of an amount of lotion sufficient to deposit about 0.5 mg/cm² of 1-(2',3',4',5'-tetramethylphenyl)-3-(propoxy)-propane- 1,3-dione to the skin prior to radiation exposure is appropriate.

EXAMPLES 5 & 6

Suntan creams are prepared by combining the following components utilizing conventional mixing techniques.

| Component | Percent by Weight Composition | |
|---|---|---|
| | Example 5 | Example 6 |
| Mineral Oil | 20.00 | 20.00 |
| Octyl Palmitate | 10.00 | 10.00 |
| Glyceryl Isostearate | 4.00 | 4.00 |
| Octyl Methoxycinnamate | 7.50 | — |
| Oxybenzone | 3.00 | — |
| Polyethylene AC-617-A,AC-6-A (available from Allied Chemical) | 2.00 | 2.00 |
| Alkyl parabens | 0.30 | 0.30 |
| Glycerin | 2.00 | 2.00 |
| 1-(2',3',4',5'-tetramethylphenyl)-3-(butoxy)-propane-1,3-dione | 2.00 | 5.00 |
| Ibuprofen | 1.00 | — |
| Water | q.s. | q.s. |

These creams are useful for topical application to inhibit damage caused by radiation, particularly acute or chronic UV exposure. Use of an amount of cream sufficient to deposit about 0.5 mg/cm² and 1.2 mg/cm² of 1-(2',3',4',5'-tetramethylphenyl)-3-(butoxy)-propane-1,3-dione to the skin for Examples 6 and 7, respectively, is appropriate.

EXAMPLE 7

A suntan stick is prepared by combining the following components utilizing conventional mixing techniques.

| Component | Percent by Weight of Composition |
|---|---|
| Candelilla Wax | q.s. |
| Ozokerite Wax | 20.00 |
| Petrolatum | 20.00 |
| Lanolin | 15.00 |
| Mineral Oil | 14.85 |
| Octyl Dimethyl PABA | 4.00 |
| Benzophenone-3 | 1.00 |
| BHA (preservative: butylated hydroxy anisole) | 0.05 |
| Propylparaben | 0.10 |
| 1-(2',3',4',5'-tetramethylphenyl)-3-(pentoxy)-propane-1,3-dione | 3.00 |

This stick is useful for topical application, for example to the lips, to inhibit damage caused by radiation, particularly acute or chronic UV exposure. Use of an amount of stick sufficient to deposit about 1.0 mg/cm2 of 1-(2',3',4',5'-tetramethylphenyl)- 3-(pentoxy)-propane-1,3-dione to the lips prior to UV exposure is appropriate.

EXAMPLE 8

A suntan cream is prepared by combining the following components utilizing conventional mixing techniques.

| Component | Percent by Weight of Composition |
|---|---|
| Tetrasodium EDTA | 0.05 |
| Alkylparabens | 0.30 |
| Carbopol (polyacrylic acid polymer-commercially available from B. F. Goodrich Chemical) | 0.20 |
| Glycerin | 2.00 |
| Laureth-23 (polyethylene glycol ether of lauryl alcohol) | 3.00 |
| Sorbitan Stearate | 1.50 |
| Octyl Dimethyl PABA | 3.00 |
| Dimethicone | 2.00 |
| Stearyl Alcohol | 6.00 |
| Triethanolamine | 0.20 |
| 1-(2',3',4',5'-tetramethylphenyl)-3-(methoxy)-propane-1,3-dione | 1.50 |
| Water | q.s. |

This cream is useful for topical application to inhibit damage caused by radiation, particularly acute or chronic UV exposure. Use of an amount of cream sufficient to deposit about 0.2 mg/cm$^2$ of 1-(2',3',4',5'-tetramethylphenyl)-3-(methoxy)-propane- 1,3-dione to the skin prior to UV exposure is appropriate.

EXAMPLE 9

A suntan aqueous face gel is prepared by combining the following components utilizing conventional mixing techniques.

| Component | Percent by Weight of Composition |
|---|---|
| Water | 50.00 |
| Aloe | 38.00 |
| Carbopol | 1.00 |
| Glycerin | 3.00 |
| Methylparaben | 0.20 |
| Triethanolamine | 0.90 |
| 2-Phenylbenzimidazole-5-sulfonic acid | 2.00 |
| Octoxynol-13 (ethoxylated alkyl phenol $(C_8H_{17})(C_6H_4)(OCH_2CH_2)_nOH$, n = average value of 13) | 1.50 |
| 1-(2',3',4'-trimethylphenyl)-3-(ethoxy)-propane-1,3-dione | 3.00 |
| Color and Fragrance | q.s. |

This aqueous gel is useful for application to the face to inhibit damage caused by radiation, particularly acute or chronic UV exposure. Use of an amount of gel to deposit about 0.5 mg/cm$^2$ of 1-(2',3',4'-trimethylphenyl-3-(ethoxy)-propane- 1,3-dione to the face prior to UV exposure is appropriate.

EXAMPLE 10

A suntan gel is prepared by combining the following components utilizing conventional mixing techniques.

| Component | Percent by Weight of Composition |
|---|---|
| Ozokerite Wax | 10.00 |
| Paraffin | 10.00 |
| Petrolatum | 10.00 |
| Isopropyl Myristate | 5.00 |
| Mineral Oil | 58.00 |
| Octyl Methoxycinnamate | 2.50 |
| Propylparaben | 0.10 |
| BHA | 0.05 |
| 1-(2',3',4',5'-tetramethylphenyl)-3-(hexoxy)-propane-1,3-dione | 4.00 |
| Naproxen | 2.00 |
| Fragrance and Color | q.s. |

This suntan gel is useful for topical application to inhibit damage caused by radiation, particularly acute or chronic UV exposure. Use of an amount of gel to deposit about 0.5 mg/cm$^2$ of 1-(2',3',4',5'-tetramethylphenyl)-3-(hexoxy)-propane-1,3-dione to the skin is appropriate.

EXAMPLE 11

A suntan oil is prepared by combining the following components utilizing conventional mixing techniques.

| Component | Percent by Weight of Composition |
|---|---|
| Sesame Oil | 5.0 |
| Cyclomethicone | 20.0 |
| Isopropyl Myristate | 5.0 |
| BHA | 0.05 |
| Sorbitan Oleate | 1.0 |
| Octyl Methoxycinnamate | 1.5 |
| Propylparaben | 0.7 |
| 1-(2',3',4',5'-tetramethylphenyl)-3-(ethoxy)-propane-1,3-dione | 2.50 |
| Mineral Oil | q.s. |

This suntan oil is useful for topical application to inhibit damage caused by radiation, particularly acute or chronic UV exposure. Use of an amount of oil sufficient to deposit about 0.8 mg/cm of 1-(2',3',4',5'-tetramethylphenyl)-3-(ethoxy)-propane- 1,3-dione to the skin prior to UV exposure is appropriate.

EXAMPLE 12

A moisturizing oil-in-water-in-silicone sunscreen emulsion lotion is formed from the following ingredients.

| Ingredient | Percent by Weight of Composition |
|---|---|
| Aqueous Phase: | |
| Water | 58.32 |
| Pantethine, 80% aq. soln. (humectant) | 0.10 |
| Methylparaben | 0.20 |
| Carbomer viscosity control agent (commercially available in the Acritamer series from R.I.T.A. Corp.) | 0.10 |
| Glycerin | 2.50 |
| Sodium alkyl polyether sulfonate (anionic emulsifier) | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.20 |
| Ethylparaben | 0.10 |
| Propylparaben | 0.15 |
| Neutralizer Base: | |
| Triethanolamine | 0.10 |

23
-continued

| Ingredient | Percent by Weight of Composition |
|---|---|
| Color & Fragrance: | |
| FD&C Red No. 4 (1% aq. soln.) | 0.03 |
| Odorant Oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (polyethylene glycol ester of a mixed synthetic $C_{11}$–$C_1$ % fatty alcohol, av. 3 moles EO) | 2.00 |
| Octyl Methoxycinnamate | 7.00 |
| Benzophenone-3 | 0.50 |
| Naproxen | 2.00 |
| 1-(2',3',4',5'-tetramethylphenyl)-3-(methoxy)-propane-1,3-dione | 2.00 |
| $C_{12}$–$C_1$ % Alcohols Benzoate | q.s. |

In a suitably sized vessel equipped with a suitable mechanical stirrer (Tekmar Model RW-20 stirring motor, manufactured by IKA-WERK, Germany), the water, pantethine, methylparaben, glycerine and sulfonate emulsifier are heated to about 72°–75° C. and mixed. Stirring is increased until a vortex forms in the aqueous solution. The thickener, Carhomer, is slowly added to the vortex and allowed to mix until completely hydrated and the resultant gel solution is free of gelatinous particles and is uniform in composition. The temperature is maintained at about 72°–75° C. with constant agitation.

The oil phase ingredients are added to a separate suitably sized vessel and heated to about 80°–85° C. using slow mechanical stirring once the oil phase becomes molten. At this point the sunscreening agents, naproxen, and 1-(2',3',4', 5'-tetramethylphenyl)- 3-(methoxy)-propane-1,3-dione are mixed in. When molten, agitation is maintained to keep the oil phase uniform during heating.

The heated oil phase is then slowly added to the heated water phase with stirring to form the oil-in-water emulsion. After addition is complete, the mechanical stirring means is slowed to avoid unnecessary aeration of the emulsion and mixing is continued for approximately fifteen minutes at 70°–75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous oil-in-water emulsion is then cooled to about 45°–50° C. and the colorant and odorant oil are added followed by cooling to room temperature (about 25° C.) with continued moderate agitation.

The four silicone fluids and other silicone phase ingredients are mixed together in a separate vessel until a uniform silicone phase is attained. The oil-in-water emulsion is slowly added to the silicone phase with stirring until a homogeneous oil-in-water-in-silicone double emulsion in lotion form is attained.

This moisturizing lotion is useful for topical application to inhibit damage caused by radiation, particularly acute or chronic UV exposure. Use of an amount of lotion sufficient to deposit about 0.5 mg/cm² of 1-(2',3',4',5'-tetramethylphenyl)-3 -(ethoxy)-propane-1,3-dione to the skin is appropriate. This lotion may also be applied several times daily, e.g., 2 or 3 times daily, for extended periods of time, i.e., greater than one week, in amounts sufficient to deposit about 0.5 mg/cm² of 1-(2',3',4',5'-tetramethylphenyl)- 3-(ethoxy)-propane-1,3-dione to the skin to inhibit damage caused by chronic UV exposure.

EXAMPLE 13

A skin conditioning toilet bar is prepared from the following ingredients.

| Component | Percent by Weight Composition |
|---|---|
| Tallow/Coconut Soap (50/50) | 61.61 |
| Water | q.s. |
| 2-Hydroxypropylglyceryl Ether | 4.00 |
| Sodium Coconut Glyceryl Ether Sulfonate | 8.80 |
| Coconut Fatty Acid (CnFA) | 4.00 |
| 1-(2',3',4',5'-tetramethylphenyl)-3-(pentoxy)-propane-1,3-dione | 2.50 |
| Perfume | 1.40 |
| NaCl | 1.04 |
| $Na_2SO_4$ | 0.34 |
| $Na_4EDTA$ | 0.06 |
| $TiO_2$ | 0.20 |
| Jaguar C15 (guar hydroxypropyltrimonium chloride) | 1.00 |
| Merquat 550 (poly quaternium-7) | 1.00 |
| Minors (Colorants, Preservatives, Fillers, etc.) | 1.55 |

The above composition is prepared in the following manner.

Crutching Step

About 127.6 parts of a mix containing: 29.8% water, 52.7% 50/50 tallow/coconut (T/Cn) soap, 16.7% sodium coconut glyceryl ether sulfonate paste, 3.3% coconut free fatty acid (CnFA), 3.1% 2-hydroxypropylglyceryl ether, and 0.2% NaCl are heated to ca. 150°–200° F. (65°–94° C.). About 10.0 parts of the hydrated polymer JAGUAR C-15 are mixed in. The1-(2',3',4',5-tetramethylphenyl)-3-(pentoxy)-propane- 1,3-dione is then added and mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part $TiO_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°–105° F. (29°–41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then stamped on a conventional soap stamping apparatus to yield the finished toilet soap bar.

The use of this toilet bar for cleansing provides a useful means for deposition of 1-(2',3',4',5'-tetramethylphenyl)-3-(ethoxy)-propane-1,3-dione to the skin to inhibit damage caused by radiation, particularly acute or chronic UV exposure. Use of the toilet bar such that about 0.05 mg/cm$^2$ of 1-(2',3',4',5'-tetramethylphenyl)-3-(ethoxy)-propane- 1,3-dione is deposited on the skin is appropriate.

EXAMPLE 14

Facial Cleanser

A facial cleanser (lathering mousse composition) is prepared from the following ingredients.

| Emulsion Concentrate (A) | Percent by Weight of Composition |
|---|---|
| DRO Water[1] | q.s. |
| 2-Hydroxypropyglyceryl Ether | 15.00 |
| Sodium Glyceryl Ether Sulfonate (90% Coconut/10 Tallow)-50% Active | 12.06 |
| Sodium Lauroyl Sarcosinate - 33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |
| Citric Acid | 0.30 |
| 1-(2',3',4'-trimethylphenyl)-3-(methoxy)-propane-1,3-dione | 1.50 |
| Jaguar C14-S (guar hydroxypropyltrimonium chloride) | 0.25 |
| Perfume | 0.20 |
| FD&C Red Dye #4 | 0.20 |
| Lauryl Alcohol | 0.20 |
| Alkyl Parabens | 0.30 |
| Germall 115 (Imidazolidinyl urea) | 0.10 |
| Na$_4$EDTA | 0.10 |
| [1]Water purified by double reverse osmosis | |

A-46 Propellant (Isobutane-Propane) (B)

(6.4 g in 100 g concentrate)

The composition is prepared in a single batch process. DRO water is brought to 71.1° C. and the Jaguar polymer is added with agitation. Maintaining agitation, the following ingredients are added sequentially: Sodium glycerol ether sulfonate, Sodium lauroyl sarcosinate, lauryl alcohol, PEG-600, Parabens, EDTA, dye, 2-Hydroxypropylglyceryl ether, stearic acid, Aloe Vera Gel, citric acid and 1-(2',3',4'-trimethylphenyl)- 3-(methoxy)-propane-1,3-dione. The mixture is then cooled to 135° –140° F. and the following ingredients are added sequentially with stirring: Lexein, Germall and perfume. The resulting mixture is cooled to room temperature.

Aluminum cans are then filled with the cooled emulsion concentrate. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin for cleansing and as a means for deposition of 1-(2',3',4'-trimethylphenyl)-3-(methoxy)-propane- 1,3-dione to the skin to inhibit damage caused by radiation, particularly acute or chronic UV exposure. Use of amount of facial cleanser sufficient to deposit about 0.05 mg/cm$^2$ of 1-(2',3',4'-trimethylphenyl)-3-(methoxy)-propane-1,3-dione to the skin is appropriate.

EXAMPLE 15

A cream soap is prepared by combining the following ingredients as described below.

| Component | Percent by Weight of Composition |
|---|---|
| Sodium Lauroyl Glutamate (Acylglutamate LS-11) (28) | 22.00 |
| Sodium Hydrogenated Tallow Glutamate and Cocoyl Glutamate (Acylglutamate GS-11) (28) | 3.00 |
| Polyethylene Glycol 400 | 10.00 |
| Polyethylene Glycol (M.W. 6300) Monostearate | 5.00 |
| Polyoxyethylene (20) Sorbitan Monostearate | 3.00 |
| 1-(2',3',4',5'-tetramethylphenyl)-3-(ethoxy)-propane-1,3-dione | 3.00 |
| Tocopherol Sorbate | 5.00 |
| Flufenamic Acid | 2.00 |
| 2-Ethylhexyl Methoxycinnamate | 3.00 |
| Water | 30.50 |
| Glycerin | 10.00 |
| Fragrance and Preservative | q.s. |

The sodium glutamate, sodium hydrogenated tallow glutamate and cocoyl glutamate, polyethylene glycol, polyethylene glycol monostearate, polyoxyethylene sorbitan monostearate, 1-(2',3',4',5'-tetramethylphenyl)-3-(ethoxy)-propane-1,3-dione, tocopherol sorbate, flufenamic acid, 2-ethylhexyl methoxycinnamate, and water are dissolved together with heating. The glycerin is added with agitation. The mixture is cooled to about 60° C. and the fragrance and preservative are added. The mixture is cooled to 35° C. with agitation.

The result is a cream soap the use of which for cleansing provides a useful means for deposition of 1-(2',3',4',5'-tetramethylphenyl)-3-(ethoxy)-propane-1,3-dione to the skin to inhibit damage caused by radiation, particularly acute or chronic UV exposure. Use of an amount of cream soap sufficient to deposit about 0.05 mg/cm$^2$ of 1-(2',3',4',5'-tetramethylphenyl)-3-(ethoxy)-propane-1,3-dione to the skin is appropriate.

EXAMPLE 16

A shampoo composition is made by combining the following components.

| Component | Percent by Weight of Composition |
|---|---|
| Ammonium Lauryl Sulfate | 12.0 |
| Ammonium Xylene Sulfonate | 2.2 |
| Ammonium Laureth Sulfate | 4.0 |
| NaCl | 0.5 |
| 1-(2',3',4'-trimethylphenyl)-3-(ethoxy)-propane-1,3-dione | 2.00 |
| Octyl Dimethyl PABA | 7.0 |
| Water | q.s. |
| Perfume and Minor Ingredients | 1.2 |

The ammonium lauryl sulfate, ammonium laureth sulfate, and ammonium xylene sulfonate are first mixed together. The 1-(2',3',4',5'-tetramethylphenyl)-3-(ethoxy)-propane-1,3-dione and octyl dimethyl PABA and perfume and minor ingredients are added and the resulting mixture is agitated in a TeckmarR Mill set at 70 for 2 minutes at 70° C.

The resulting shampoo composition is added to hair which has been wetted with water, worked through the hair then rinsed out. This allows for deposition of 1-( 2',3',4',5'- tetramethylphenyl)-3-(ethoxy)-propane-1,3-dione and octyl dimethyl PABA to the scalp to inhibit damage caused by acute or chronic UV exposure. Use of an amount of shampoo sufficient to deposit about 0.05 mg/cm² of 1-(2',3',4'-trimethylphenyl)- 3-(ethoxy)-propane-1,3-dione to the scalp is appropriate.

EXAMPLES 17 & 18

Simple solutions are made by combining the following components:

|  | Percent by Weight of Composition | |
| --- | --- | --- |
|  | Example 17 | Example 18 |
| Propylene glycol | 27.6 | 28.5 |
| Ethanol, absolute | 46.1 | 47.5 |
| Water | q.s. | q.s. |
| 1-(2',3',4',5'-tetramethylphenyl)-3-(ethoxy)-propane-1,3-dione | 3.00 | 1.50 |

The propylene glycol, ethanol and water are first mixed together in proportions of 25:55:20 v:v:v, respectively. This solution is then combined with 1-(2',3',4',5'-tetramethylphenyl)- 3-(ethoxy)-propane-1,3-dione in proportions of 95:5 w:w for Example 18 and 98:2 w:w for Example 19 to produce the final solutions. Topical application of these solutions in an amount sufficient to deposit about 0.2 mg/cm² for Example 18 and 0.07 mg/cm² for Example 19 of 1-(2',3',4',5'-tetramethylphenyl)-3 -(ethoxy)-propane-1,3-dione to the skin inhibits damage caused by radiation, particularly acute or chronic UV exposure.

While particular embodiments of the subject invention have been described, it will be obvious to those skilled in the art that various changes and modifications of the subject invention can be made without departing from the spirit and the scope of the invention. It is intended to cover, in the appended claims, all such modifications that are within the scope of this invention.

What is claimed is:

1. A photoprotective composition comprising:
   a) A safe and effective amount of a compound having the structure:

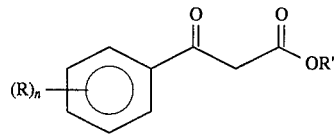

wherein n is 3 or 4; each R is, independently, linear or branched, substituted or unsubstituted, saturated or unsaturated $C_1$–$C_5$ alkyl or alkoxy; and R' is linear, branched or cyclic, substituted or unsubstituted, saturated or unsaturated $C_1$–$C_{20}$ alkyl, wherein when R' is substituted, the substituent(s) is selected from the group consisting of halogen, hydroxy, amino, nitro, carboxy, thio, aryl, alkyl, alkoxy, and aryloxyl; and (b) a pharmaceutically-acceptable topical carrier.

2. The composition of claim 1 wherein R is $C_1$–$C_4$ alkyl.
3. The composition of claim 2 wherein R' is $C_1$–$C_8$, saturated alkyl.
4. The composition of claim 3 wherein R' is unsubstituted.
5. The composition of claim 4 wherein n is 4.
6. The composition of claim 4 wherein R is saturated $C_1$–$C_2$ alkyl.
7. The composition of claim 6 wherein R is methyl.
8. The composition of claim 7 wherein n is 4.
9. The composition of claim 7 wherein R' is $C_1$–$C_4$ alkyl.
10. The composition of claim 8 wherein R' is $C_1$–$C_2$ alkyl.
11. The composition of claim 10 wherein R' is methyl.
12. The composition of claims 1, 8 or 11 wherein the composition comprises from about 0.5% to about 10% of the compound and from about 5% to about 20% of an emollient.

* * * * *

UNITED STATES PATENT AND TRADEMARK OFFICE
CERTIFICATE OF CORRECTION

PATENT NO. : 5,492,690
DATED : February 20, 1996
INVENTOR(S) : Rodney D. Bush

It is certified that error appears in the above-indentified patent and that said Letters Patent is hereby corrected as shown below:

Column 13, line 20, " Sunscreens     " should read --Sunscreens and Sunblocks--.

Signed and Sealed this

Eleventh Day of February, 1997

Attest:

BRUCE LEHMAN

Attesting Officer        Commissioner of Patents and Trademarks